United States Patent [19]

Daly et al.

[11] 4,337,776

[45] Jul. 6, 1982

[54] IMPEDANCE MEASURING PACER

[75] Inventors: Christopher N. Daly, Bilgola Plateau; Michael S. Hirshorn, Darling Point; David K. Money, Pennant Hills; Loraine K. Holley, Rockdale, all of Australia

[73] Assignee: Telectronics Pty. Ltd., Australia

[21] Appl. No.: 182,820

[22] Filed: Aug. 29, 1980

[51] Int. Cl.³ .............................................. A61N 1/36
[52] U.S. Cl. ............................................ 128/419 PT
[58] Field of Search .................. 128/419 PT, 419 PG

[56] References Cited

U.S. PATENT DOCUMENTS

| | | | |
|---|---|---|---|
| 3,669,120 | 6/1972 | Nielsen | 128/419 PT |
| 3,756,246 | 9/1973 | Thaler et al. | 128/419 PT |
| 3,777,762 | 12/1973 | Nielsen | 128/419 PT |
| 3,800,801 | 4/1974 | Gaillard | 128/419 PT |
| 3,845,773 | 11/1974 | Fontaine | 128/419 PG |
| 3,857,085 | 12/1974 | Mulier et al. | 128/419 PT |
| 3,949,758 | 4/1976 | Jirak | 128/419 PT |
| 4,102,345 | 7/1978 | Cannon | 128/419 PT |
| 4,245,643 | 1/1981 | Benzing et al. | 128/419 PT |

OTHER PUBLICATIONS

Furman et al. "Medical Research Engineering" Third Qtr. 1967, pp. 29-32.

Primary Examiner—William E. Kamm
Attorney, Agent, or Firm—Gottlieb, Rackman & Reisman

[57] ABSTRACT

A pacer which facilitates the measurements of both electrode impedance and stimulation threshold. When activated by an external magnet, a sequence of reducing-amplitude stimulating pulses is generated, with successive pulses in the sequence being separated by full-amplitude pulses. This pulse alternation scheme allows long test sequences, and therefore measurements with greater resolution, because full-amplitude pacing pulses are always present (even though at a slightly reduced rate). The reduction in amplitude of successive pulses is determined by the electrode impedance rather than being predetermined, and thus the examination of a skin potential recording allows electrode impedance to be determined along with the capture threshold.

25 Claims, 9 Drawing Figures

IMPEDANCE MEASURING PACER

This invention relates to pacers which facilitate the measurements of electrode impedance and stimulation threshold, and more particularly to such pacers which allow high-resolution measurements without compromising patient safety.

There are several pacers on the market which allow a patient's stimulation threshold to be determined. In the Vario pacer, manufactured by the Siemens-Elema Company, the pacer output pulse amplitude is reduced in sixteen equal incremental steps from full amplitude to zero, following the activation of a test cycle by the placing of a magnet on the patient's chest over the pacer. The voltage at which capture is lost, as a percentage of maximum pulse amplitude, can be determined from a surfae electrocardiogram by counting the number of pulses from the start of the test cycle until the pulse which no longer results in a heartbeat signal on the EKG trace.

Although the threshold value, as evident from an EKG trace, is necessarily a percentage of the maximum pulse amplitude, the exact threshold value—to within the accuracy of the system—can be determined by measuring the maximum pulse amplitude. For many pacers on the market the pacer rate varies as a function of the battery potential which determines the maximum pulse amplitude; thus the maximum amplitude can be determined from the rate, and from that level the threshold value can be calculated.

The limiting factor in the measurement accuracy is the number of steps in which the pulse amplitude is reduced to zero. Because the test cycle can leave the patient unpaced for the period between the loss of capture and the end of the cycle, the time allowed for the pulse height to reduce down to zero must be limited. It is apparent that if capture is lost following the first reduction in pulse amplitude, fifteen heartbeats may be missed. Even though the test sequence is carried out at a fixed rate which is slightly higher than that to which the pacer is set to operate, it has not been practical in the prior art to increase the number of pulses in the test cycle in any way which provides significantly increased measurement resolution.

A considerable amount of work has been done in the area of providing stimulation threshold measurements. For example, instead of allowing the reducing-amplitude test pulses to continue after capture is lost until the end of the test cycle, it is possible to terminate the test cycle, and to restore full-amplitude pulses by removal of the magnet or automatically, as soon as the pacer determines that a heartbeat did not follow the generation of a stimulating pulse. Another variation, found in some Vitatron Medical pacers, involves reducing the pulses in the test sequence by a fixed incremental value in groups of four; four pulses at maximum amplitude are generated, followed by four pulses whose amplitude is 0.5-volts less, followed by four pulses whose amplitude is 0.5-volts still less, etc. Two early patents in the field are U.S. Pat. Nos. 3,669,120 and 3,777,762, both issued to Lars Stig Nielsen respectively on June 13, 1972 and Dec. 11, 1973. The former patent is particularly pertinent to our invention because it suggests, although does not disclose, the generation of full-amplitude pulses between the pulses of reducing amplitude (see Column 3, lines 32–38). The advantage of such a scheme is not stated nor is any way suggested for doing the job.

We have discovered, however, a significant practical reason for providing full-amplitude pulses between successive pulses of reducing amplitude in the test sequence. Unless a special mechanism is provided for terminating the test sequence as soon as capture is lost, the number of pulses in the test sequence must be limited, as described above, in order that the patient not be without a pacing function for too long a time period. This, in turn, limits the resolution of the measurement because relatively large amplitude decrements must be employed; the 0.32-volt decremental difference between pulses in the Siemens-Elema test sequence, for example, is insufficient for a detailed study of stimulation threshold. (The newer Siemens MultiProgrammable pacer allows 0.16-volt decrements.) But by providing full-amplitude pulses which separate the pulses of reducing amplitude in the test sequence, the patient is in no danger of being without a pacing function no matter how long the test sequence, and thus the difference in amplitude between successive pulses may be much smaller to provide more accurate measurements. Another major advantage of providing this type of alternate pulse scheme is that if a physician inadvertently leaves the test magnet on top of a patient, thereby prolonging the test sequence indefinitely (with all of the terminal test sequence pulses having zero amplitude), there is no danger to the patient because his pacer still functions to provide stimulating pulses of full amplitude at an acceptable rate.

It is an object of our invention to provide a pacer for facilitating a stimulation threshold measurement in which a sequence of pulses having decreasing amplitudes are interspersed with full-amplitude pulses.

It is standard practice in the pacer industry to design special integrated circuits for use in a pacer. The initial high design cost is justified by greater reliability and ultimately lower costs in volume production. It might be thought that a special chip would have to be designed to implement the stimulation threshold measurement contemplated by our invention.

It is another object of our invention to utilize two chips, one for providing the normal pacer stimulating pulses and for controlling the other which provides the alternate pulses of reducing amplitude during the stimulation threshold measurement, the active circuits on the two chips being identical.

While considerable attention has been paid in the prior art to threshold measurement, fewer efforts have been devoted to measurement of electrode impedance. By "electrode impedance" is meant not only the impedance of an electrode, but also the impedances of its tip, its connection to the pacer, and body fluids and tissues, i.e., the total impedance seen by each pacer stimulating pulse. Impedance measurement is important primarily because it allows an estimate of pacer longevity and because a change in impedance may signify lead or insulation breakage, tip/terminal loosening, or tip surface alteration as a result of corrosion. It is also expected that once impedance and threshold measurements become routine, they will be useful as a basis for pacer and electrode design. For example, it is believed that impedance and threshold changes may be related to electrode tip porosity. The provision of a pacer which allows simple but accurate measurements of both threshold and electrode impedance should be instrumental in advancing the state of the art.

One method of determining electrode impedance is by careful measurement of the ratio between the leading and trailing edges of a pacer pulse, since the relative amplitudes of these edges are a function of the electrode impedance into which the pacer output capacitor discharges. But measurements made this way are inaccurate because of the poor definition of the trailing edge of a pacer pulse. It has also been proposed for an implanted pacer to measure electrode impedance and transmit the information by telemetry to a specially provided programmer. Such a system, of course, requires additional equipment.

It is another object of our invention to provide a pacer which allows direct and accurate measurement of electrode impedance from a recording of skin potentials.

It is another object of our invention to provide such a measurement of electrode impedance which is independent of the potential of the pacer battery.

It is still another object of our invention to provide such a measurement of electrode impedance at the same time that a stimulation threshold measurement is performed.

Briefly, in accordance with the principles of our invention and in the illustrative embodiment thereof, the pacer operates normally at 72 pulses per minute. Upon application of a magnet (or other means) to the skin over the pacer, the pulse rate increases to approximately 100 pulses per minute. Every other pulse is of maximum amplitude, that is, the amplitude to which the pacer is set for normal pacing. But alternate pulses get smaller and smaller. When the amplitude of the diminishing pulse sequence drops below the stimulation threshold, capture occurs on only every second pulse and the heartbeat rate is reduced to approximately 50 beats per minute. Such a rate is physiologically acceptable. As soon as the activating magnet is removed, the pulse rate reverts to 72 pulses per minute.

The threshold is determined by measuring the height of the smallest pulse on a skin potential recording which results in capture. The ratio of this pulse height to the maximum pulse height is the threshold value as a percentage of maximum amplitude. If this value is multiplied by the maximum pulse amplitude in volts, then the threshold voltage can be determined. (The maximum amplitude, in volts, is usually known during the first few years of pacer operation until there is a reduction in the battery potential. But if a threshold value in terms of a percentage of maximum amplitude is not sufficient, or if it cannot be assumed that the actual maximum amplitude is known, it can be determined from the rate which is a function of battery potential.) High-resolution measurements are possible because there is a very small difference between successive pulses; long test sequences are feasible because there is no danger that the patient will remain unpaced.

As will become apparent below, the resolution actually changes from pulse to pulse because the decremental difference between successive pulses becomes less and less; toward the end of the test cycle, successive pulses differ less than they do at the beginning of the cycle. Typically, at threshold levels in the vicinity of 3 volts, the resolution is about 0.2 volts. At threshold levels in the vicinity of 1.5 volts, the resolution is approximately 0.1 volts. Both are far better than the resolutions possible in prior art systems. (The resolutin can be further increased by increasing the values of capacitors C3-2 and C4-2 to be described below in connection with FIG. 2.)

Because the threshold cannot be determined from a standard EKG trace produced by a chart recorder, due to the limited dynamic range and speed of such recorders, it is necessary to display the EKG trace on either a storage cathode ray oscilloscope, or to utilize a high-speed recorder with the necessary dynamic range and speed to capture all of the pulses, or to employ a pacing pulse analyzer which measures the amplitudes of successive pulses. (Specially adapted EKG recorders can also be used if the peak amplitude of the pacing pulse is sampled and held, and electronically widened, so that the chart recorder has time to respond accurately.)

Electrode impedance can be determined readily from the resulting recording. All that is required is to count the number of pulses from the first pulse in the test sequence until the pulse amplitude is reduced by 90% of its initial value. A chart may be provided with the pacer which lists electrode impedance for each such pulse count number. Once the pulse count number for a 90% pulse-amplitude reduction is determined, the impedance is readily determined from the chart.

The reason that this technique works will be explained in detail below, but what is important is that successive pulses in the reducing-amplitude sequence not differ by a fixed decremental value or even a varying decremental value which is determined by the pacer itself. Instead, each decrement is a constant percentage of the amplitude at the trailing edge of the preceding pulse, and the value of the percentage is determined by the electrode impedance to be measured. Thus if the constant percentage difference is 10%, and some pulse has an amplitude of 4.000 volts, the next pulse will have an amplitude of 3.600 (4.000−0.400) volts, the next one will have an amplitude of about 3.240 (3.600−0.360) volts, etc. This is the key to the electrode impedance measurement, a measurement which as it turns out is not even dependent upon battery potential.

The pacer of our invention employs an integrated circuit of the type used in the past for pacers not provided with threshold or impedance measurement capabilities. The chip is used for the basic pacer functions. But another chip, with the identical active circuits, is employed to provide the additional capabilities of the pacer of our invention. This second chip is under control of the first, and due to unique circuit connections allows a chip designed for one purpose to be used for a completely different purpose.

Further objects, features and advantages of our invention will become apparent upon consideration of the following detailed description in conjunction with the drawing, in which:

FIGS. 1 and 2, with FIG. 1 being placed on top of FIG. 2, depicts the illustrative embodiment of our invention;

One of the advantages of the illustrative embodiment of the invention is that it may be implemented without requiring specially designed chips. For reasons of reliability and in order to reduce the physical size of a pacer, it is common practice to design special integrated circuits, each of which performs respective functions; the initial design cost is justified, not only by the greater reliability and smaller size, but eventually by reduced cost with increasing volume. It would be particularly advantageous to implement a threshold/impedance measuring pacer without requiring the design of any chips other than those used in pacers without the measurement capability.

Figure 1:
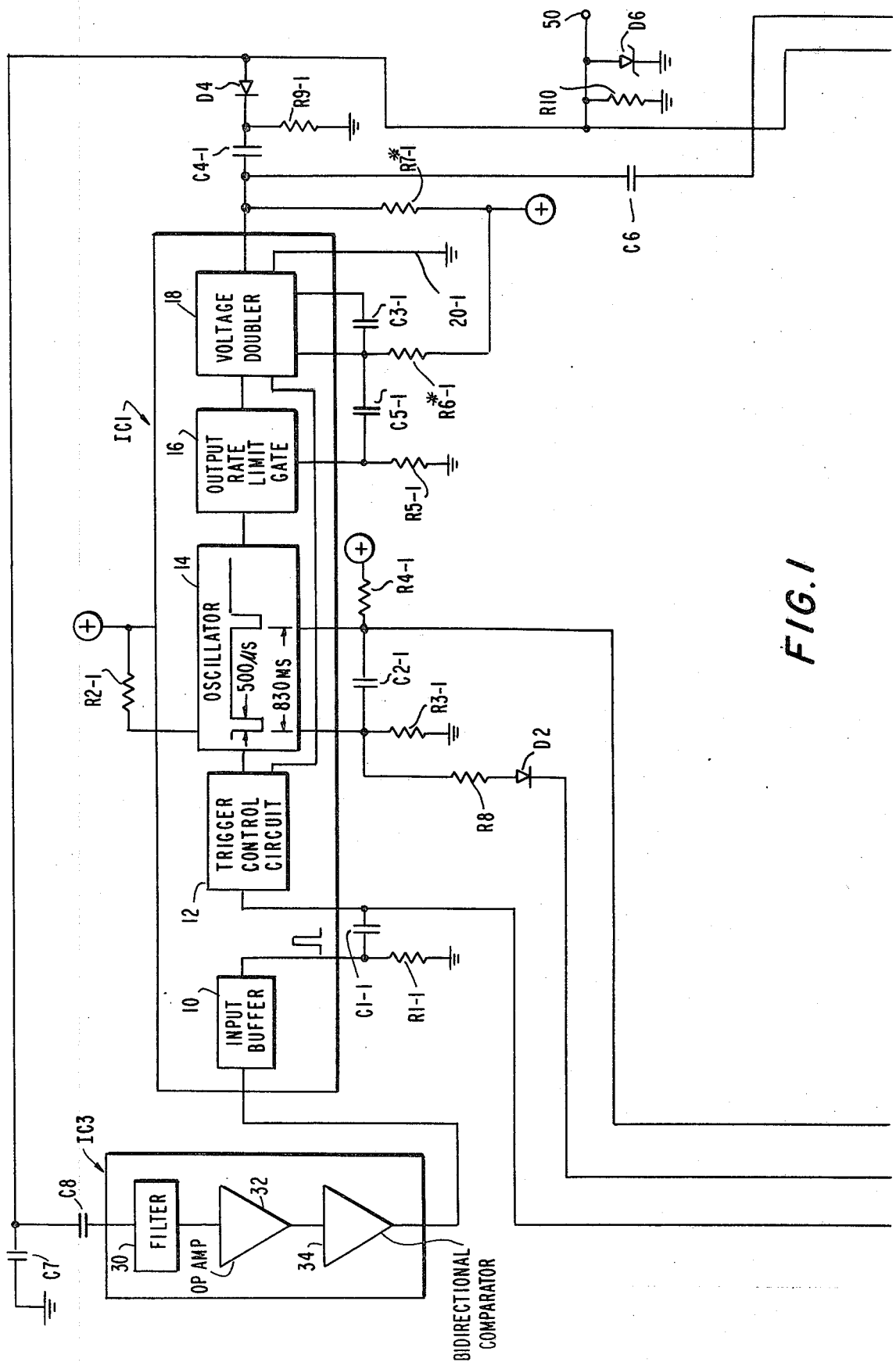
Figure 2:
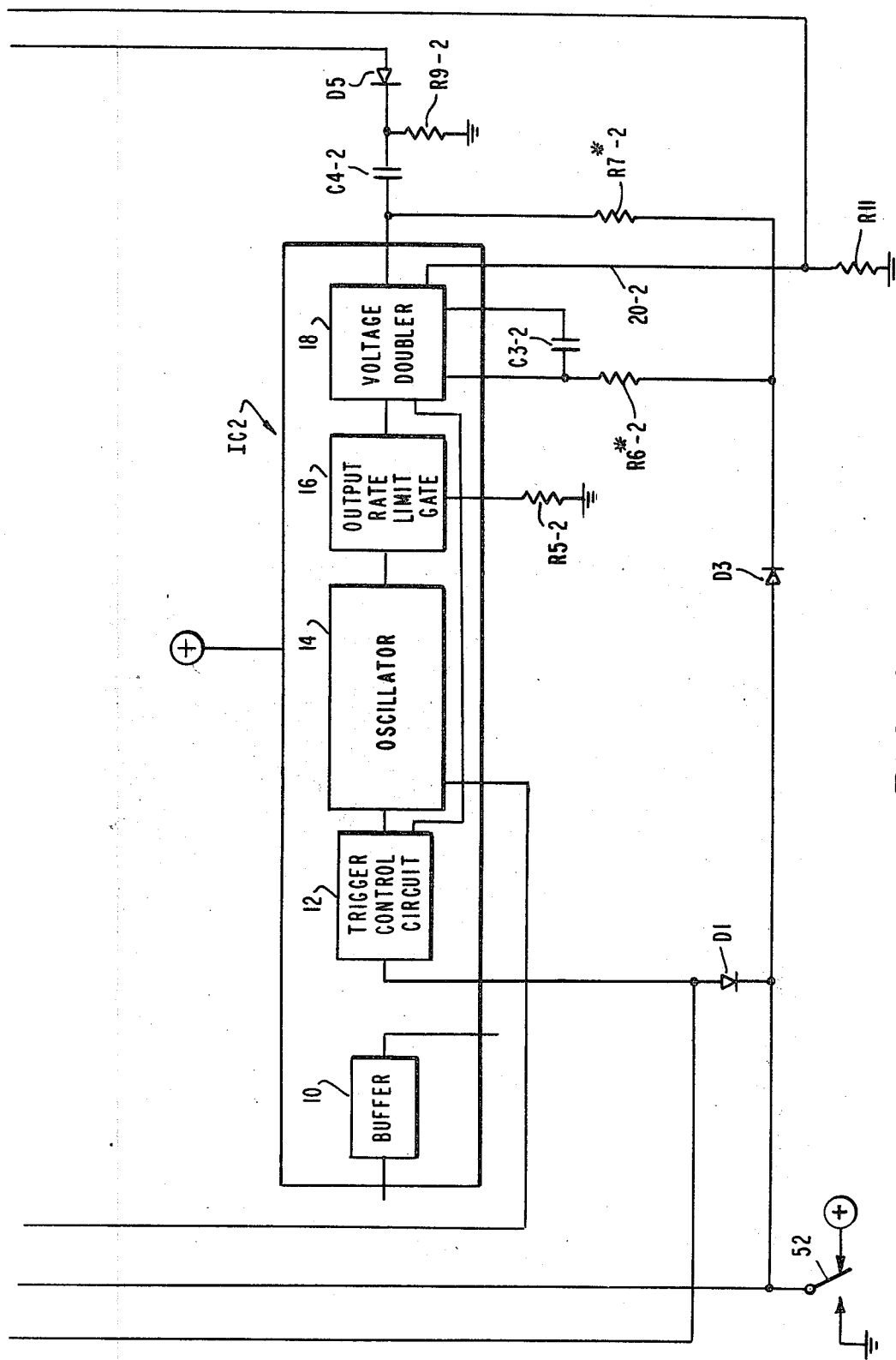

In the illustrative embodiment of the invention, the pacer uses two identical chips, IC1 on FIG. 1 and IC2 on FIG. 2. Chip IC1 is the "heart" of a conventional pacer without the measurement capability. In order to appreciate how the use of a second identical chip can give rise to an altogether different function, it is first necessary to review a basic pacer circuit not having the measurement capability. Such a pacer is actually depicted in FIG. 1. All that is required is to ignore the conductors extended to FIG. 2, and to omit the connected components—resistor R8, diode D2 and capacitor C6. (Also, diode D4 should be considered to be shorted, since this diode is necessary only when chip IC2 is used, as will be described below.)

The basic pacer includes two chips, IC1 and IC3, and connected discrete components. The chips include all active components (transistors). Chip IC3, which is shown in symbolic form only since the detailed circuitry involved is well known to those skilled in the art, serves to detect a signal on electrode 50 resulting from a spontaneous heartbeat, and to process the signal in order to control properly timed stimulating pulses. (Terminal 50 in the drawing represents the electrode.) Capacitor C8 couples the input signal to chip IC3, and capacitor C7 is a high-frequency by-pass capacitor which aids chip IC3 in rejecting high-frequency interference. Chip IC3 itself is shown as including a filter 30, an operational amplifier 32, and a bidirectional comparator 34. In actual practice, some of the components which determine the filter and comparator operations are external to the chip, but that is of no moment. The filter and operational amplifier together function as a bandpass amplifier with a midband gain at 45 Hz of approximately 180, an optimum configuration for intracardiac QRS detection. The bidirectional comparator causes its output to go high whenever the voltage at its input exceeds an internal reference voltage by 100 millivolts in either direction. The output of chip IC3 is extended to input buffer 10 on chip IC1; when the input to chip IC1 goes high, it is an indication that a heartbeat has occurred.

Chip IC1 is also shown in symbolic form only; detailed schematics of numerous pacers are well known in the art. The blocks shown within chip IC1, together with the connected discrete components, control respective functions. The input buffer 10 provides a high input impedance for coupling to the output of the QRS detection chip IC3, and a clamped output drive souce for resistor R1-1 and capacitor C1-1. The output, a positive pulse, is clamped to a voltage level less than that of the battery, so that the RC time constant is independent of battery potential. Each positive pulse at the output of the input buffer is extended through capacitor C1-1 to the input of trigger control circuit 12. But if input pulses arrive at too high a rate, the capacitor does not have sufficient time to discharge between successive pulses and these pulses are not transmitted through the capacitor to the trigger control circuit. The time constant is such that the pulses which occur at a rate higher than about 5–10 per second are ignored. Such high-rate pulses cannot possibly represent spontaneous beats and are more likely to arise from stray interference. By ignoring the pulses, the pacer is caused to operate in a continuous mode rather than in a demand mode, but that is better than inhibiting all pacer pulses which would otherwise be the case. (It should be noted that if the right end of capacitor C1-1 is grounded, then no pulses are applied to trigger control circuit 12 and chip IC1 will operate in a continuous mode. This is what is actually done when the chip is employed in a continuous pacer. As will be described below, during the threshold and impedance measuring operations, the right side of capacitor C1-1 is grounded so that trigger control circuit 12 does not operate.)

Oscillator 14 generates 500-microsecond negative pulses at 830-millisecond intervals, corresponding to 72 pulses per minute. Trigger control circuit 12, responsive to each pulse transmitted to it through capacitor C1-1, causes the oscillator to generate a pulse and to reset so that another 830-millisecond timing period begins. The operation of oscillator 14 is controlled by four external components, capacitor C2-1, and resistors R2-1, R3-1 and R4-1. Resistor R2-1 and the capacitor determine the pulse width, 500 microseconds in the illustrative embodiment of the invention. Resistor R3-1 and the capacitor determine the oscillator rate, 72 pulses per minute in the illustrative embodiment of the invention. Resistor R4-1 and the capacitor set the refractory period, typically 250 milliseconds. Any trigger pulse which occurs within the first 250 milliseconds following the generation of an oscillator pulse has no effect; this insures that an evoked ventricular depolarization which results from the generation of a stimulating pulse does not itself re-trigger the oscillator.

The oscillator cycle starts with the potential at the junction of capacitor C2-1 and resistor R3-1 being slightly above the batter potential. The potential drops gradually due to capacitor C2-1 discharging toward ground through resistor R3-1. When the potential reaches a preset switching threshold below the battery potential, the junction of capacitor C2-1 and resistor R4-1 is switched to ground. At the same time, resistor R2-1 is switched through to the junction of capacitor C2-1 and resistor R3-1. The left side of capacitor C2-1, through the action of the grounding switch on the right side, is now slightly below ground but rapidly recharges to a second preset switching threshold above ground. When it reaches this threshold, the switch at the junction of resistor R4-1 and capacitor C2-1 turns off, causing the right side of the capacitor to go to the battery potential and the left side to go to its original starting point of slightly above the battery potential.

The pulse interval is determined by the time required for capacitor C2-1 to discharge through resistor R3-1 to the first threshold. The pulse width is determined by the time required for the capacitor to recharge through resistor R2-1 to the second threshold.

If the trigger control circuit 12 operates before the first threshold is reached, the switch at the junction of capacitor C2-1 and resistor R4-1 is caused to operate, forcing a pulse to be generated and the oscillator to reset normally.

The actual functioning of oscillator 14 is not important for an understanding of the present invention. What is important is to appreciate that whenever an oscillator pulse is generated, a negative pulse appears at the junction of capacitor C2-1 and resistor R4-1 (since this negative pulse will be described below as controlling the operation of chip IC2). Also, whenever a low potential appears at the junction of capacitor C2-1 and resistor R3-1, the oscillator generates a pulse and resets. (This will be important when considering chip IC2 since such a potential is applied to the corresponding input of chip IC2.) Lastly, the inter-pulse interval is controlled by the R3/C2 time constant. With resistor R8 out of the circuit, an inter-pulse interval of 830 milliseconds is obtained. But, as will be described beow, if resistor R8 is coupled through diode D2 to ground, it is placed in parallel with resistor R3-1 and thus reduces the time constant. The result is a reduced inter-pulse interval.

Output rate limit gate 16 serves to block certain oscillator pulses from reaching voltage doulber 18; the output rate limit gate will be described below. The voltage doubler allows a pulse of approximately twice the battery voltage to be applied to the connected electrode. As will be described in connection with FIG. 3A, this is achieved by charging capacitors C4-1 and C3-1 in parallel, and then switching them in series when an output pulse is required. The resulting pulse is negative, and has an amplitude which is twice that of the battery. In the absence of diode D4 (or even if it is present), the two capacitors in series discharge into electrode 50 to stimulate the patient's heart. Zener diode D6 protects the pacer circuitry from externally applied voltages, e.g., during defibrilation or diathermy procedures, a standard safeguard on all pacers. Resistor R10 provides a ground reference and discharge path for the electrode, and it is also the input impedance seen by the electrode when heartbeat signals are detected.

Conductor 20-1 allows the pacer to be operated in a selected one of the "synchronous" or "inhibit" modes. The drawing does not depict how this is controlled, but the type of control is well known in the art. If conductor 20-1 is open circuited, the pacer operates in the synchronous mode—an output stimulating pulse is delivered with each oscillator pulse, whether the oscillator pulse follows an 830-millisecond time-out or results from a trigger pulse from circuit 12. In the latter case, a spontaneous beat is reinforced by the pacer. On the other hand, if conductor 20-1 is grounded, as it is in FIG. 1, then the pacer operates in the inhibit moe—an output pulse occurs only when the oscillator times out, and resetting of the oscillator by a trigger pulse does not result in pacer reinforcement of a spontaneous beat.

To provide a more complete understanding of the voltage doulber circuit 18, it includes an internal output inhibit gate. This gate is actually controlled by the "synchronous/inhibit" conductor 20-1, and also by a conductor from the trigger control circuit which is illustrated. If the synchronous/inhibit conductor is grounded, then the output circuit 18 is set for inhibited mode operation. The output inhibit gate is enabled by the trigger control circuit. If the oscillator is reset due to a trigger from trigger control circuit 12, then the oscillator pulse will not activate the output circuit 18. On the other hand, if the oscillator pulse follows a normal time-out, then the inhibit gate will not be enabled and an output pulse will be delivered. If the synchronous/inhibit conductor is left open-circuited, which it is not in FIG. 1, then the connection to the trigger control circuit is ignored so that all oscillator pulses cause an output pulse to be delivered, whether they result from a trigger or a normal time-out.

As will be described below in connection with FIG. 3A, resistors R6*-1 and R7*-1 are the resistors through which capacitors C3-1 and C4-1 recharge between output pulses. Typically, these resistors are internal to chip IC1. With the resistors being internal to the chip, an actual chip which satisfies all of the requirements for chip IC1 is the AWM 1400R, used in various Telectronics pacers. But for reasons which will become apparent below in connection with chip IC2, the two capacitor-charging resistors are external to the chip. In order to use two identical chips in the overall circuit (for accomplishing totally different functions), it would be advantageous to design only a single chip which requires two external resistors, especially for a new-generation design for which new chips are required anyway.

Output rate limit gate 16 serves to prevent output pulses from occurring at too high a rate, in the event of the oscillator rate increasing due to a component failure. Whenever the voltage doubler delivers an output pulse to the electrode, capacitor C5-1 charges. Following the trailing edge of the pulse, the capacitor discharges through resistor R5-1. But until the capacitor discharges, the potential at the junction of resistor R5-1 and capacitor C5-1 prevents pulses from oscillator 14 from being transmitted through gate 16 to voltage doubler 18. In the illustrative embodiment of the invention, it requires 780 milliseconds (corresponding to 77 pulses per minute) for capacitor C5-1 to discharge following the trailing edge of an output pulse before another oscillator pulse is permitted through gate 16. (Although a 780-millisecond interval is utilized, any interval between 580 milliseconds and 830 milliseconds would be suitable, provided a sufficient safety margin is allowed for rate variations due to battery voltage changes.) The resulting operation is depicted on the left side of FIG. 4.

The upper waveform depicts oscillator pulses occurring at the basic rate of 72 pulses per minute (830-millisecond inter-pulse intervals). The second waveform depicts the operation of the output rate limit gate. For 780 milliseconds following the trailing edge of each oscillator pulse, the waveform is low and no pulses are permitted through gate 16. When the waveform goes high following the 780-millisecond period, however, oscillator pulses can be transmitted through the gate. The left side of the third waveform depicts the output pulses from chip IC1 when chip IC2 is not included in the circuit. As long as the oscillator pulses occur with a spacing greater than 780 milliseconds, every oscillator pulse results in an output pulse.

Figure 3A:
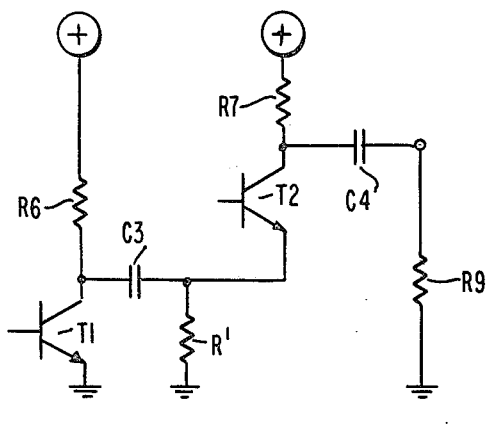
FIG. 3A depicts the output circuit in voltage doubler 18 of each of chips IC1 and IC2 on respective ones of FIGS. 1 and 2, with FIG. 3B representing the manner in which output pulses are generated on chip IC1 and FIG. 3C representing the manner in which output pulses are generated on chip IC2.

FIG. 3A depicts the manner in which capacitors C3-1 and C4-1 serve to double the battery voltage. Transistors T1 and T2 and resistor R' are internal to voltage doubler 18, with capacitors C3 and C4, and resistors R6, R7 and R9 being connected to these transistors. (In FIG. 3A, the "-1" suffixes of FIG. 1 are omitted.) Between pulses, i.e., during the 830-millisecond timing period of oscillator 14, transistors T1 and T2 are both off. Capacitor C4 charges from the battery through resistors R7 and R9, and capacitor C3 charges from the battery through resistors R6 and R'. Thus the left side of capacitor C4 and the left side of capacitor C3 are both positive, with the right side of each capacitor being grounded after the capacitor is fully charged. But whenever an oscillator pulse is generated and the pulse is transmitted through gate 16, transistors T1 and T2 turn on. At this time the two capacitors are connected in series with the two collector-emitter circuits of transistors T1 and T2, and the output electrode. Because it is the left sides of the capacitors which are positive relative to the right sides, and because they are connected in series with the left side of capacitor C3 being connected to ground through transistor T1, it is apparent that the output potential is negative and is equal to twice the battery voltage.

Figure 3B:
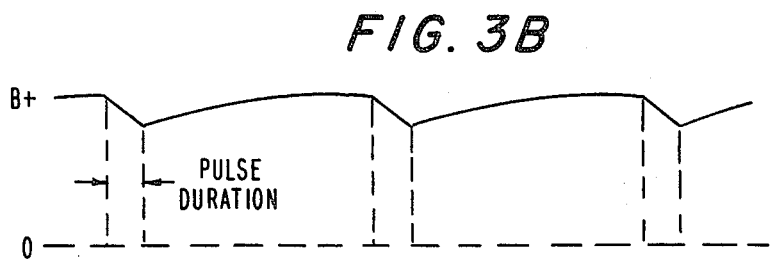

FIG. 3B depicts the potential across each of the capacitors. During the generation of a stimulating pulse, when transistors T1 and T2 turn on, each capacitor discharges and its potential decreases from B+ towards zero. The capacitors do not fully discharge, however, and at the end of the pulse, when transistors T1 and T2 turn off, the two capacitors start charging once again, the voltage across each capacitor rising to the full battery potential.

With this description of a basic prior art type pacer in mind, reference should now be made to the overall circuit depicted in FIGS. 1 and 2. Chip IC2 is identical to chip IC1. (As mentioned above, while resistors R6*-1 and R7*-1 may be internal to chip IC1, the corresponding resistors for chip IC2 should be external, and in the illustrative embodiment of the invention the resistors are external even for chip IC1.) Reed switch 52 is shown in its normal position; the switch changes state when an external magnet is placed over the chest of the patient. With the switch in its normal position, diode D1 is reverse biased. The anode of the diode is connected to the input of trigger control circuit 12 in each of chips IC1 and IC2, but because the diode is reversed biased it has no effect on the circuit operation.

The switch is also connected to the cathode of diode D2, but when it is in its normal position the diode is effectively out of the circuit as described above in connection with the operation of chip IC1.

Diode D3 is forward biased during normal pacing, and voltage doubler 18 in chip IC2 could otherwise operate as does the voltage doubler in chip IC1. However, the output of chip IC1 is connected through capacitor C6 to resistor R11 and the synchronous/inhibit control input of chip IC2. It will be recalled that conductor 20-1 connected to chip IC1 is grounded so that this chip operates in the inhibit mode. As will be described below, oscillator 14 in chip IC2 emits pulses in response to those from oscillator 14 in chip IC1. Thus an output pulse would otherwise be emitted by chip IC2 whenever an output pulse is generated by chip IC1. But because each negative pulse from chip IC1 is coupled to conductor 20-2, whenever chip IC2 would otherwise emit an output pulse together with the output pulse from chip IC1 it does not do so because it is switched to operate in the inhibit mode. Thus during normal pacing operation, no pulses are emitted by chip IC2.

The circuit components could be selected such that the magnitude of the output pulses from chip IC1 is always greater than that of the pulses from chip IC2. (When same-magnitude components are associated with the two chips, the output pulse from chip IC1 is in fact always greater than that from chip IC2 because diode D3, which is in series with resistors R6*-2 and R7*-2, causes the voltages on capacitors C3-2 and C4-2 to be less than those on capacitors C3-1 and C4-1.) Since diodes D4 and D5 are connected back-to-back (to isolate capacitors C4-1 and C4-2 from the electrode except when negative stimulating pulses are generated), the larger negative potential of the output of chip IC1 would reverse bias diode D5, and chip IC2 would be prevented from extending pulses to electrode 50. However, there might still be a waste of energy due to the switching which takes place in voltage doubler 18 in chip IC2. By preventing even this switching (i.e., by enabling the output inhibit gate in chip IC2, independent of its trigger control circuit, whenever chip IC1 generates an output pulse), there is no drain on the battery during ordinary pacing.

When the pacer is operated in the measurement mode, reed switch 52 changes position. Diode D3 is reverse biased, and capacitors C3-2 and C4-2 do not charge between pulses from the battery. This is the key to achieve a reducing pulse amplitude for alternate pulses. The ground potential on switch 52 is also extended through diode D1 to the input of trigger control circuit 12 in chip IC1. By grounding the input, the oscillator on chip IC1 operates in a continuous mode, oscillator pulses being generated independent of QRS detection. There is no connection to input buffer 10 on chip IC2. As will be described below, oscillator 14 in chip IC2 is responsive to oscillator 14 in chip IC1. To ensure that oscillator 14 in chip IC2 is not affected by anything other than the oscillator in chip IC1, the anode of diode D1 is also coupled to the input of the trigger control circuit in chip IC2. (During normal pacing, trigger control circuit 12 in chip IC2 performs a function performed by trigger control circuit 12 in chip IC1; QRS detection results in input buffer circuit 10 in chip IC1 causing both trigger control circuits to enable their output inhibit gates. Otherwise, a detected QRS signal, while inhibiting a pulse from chip IC1, would result in chip IC2 emitting a pulse since oscillator 14 in chip IC2 emits a pulse. Chip IC2 does not deliver a pulse, however, because its trigger control circuit 12 enables its output inhibit gate.)

With switch 52 grounded, diode D2 conducts and resistor R8 is connected in parallel with resistor R3-1. As described above, this has the effect of reducing the inter-pulse interval of oscillator 14 in chip IC1. The inter-pulse interval is reduced from 830 milliseconds to 580 milliseconds (corresponding to 103 pulses per minute) in the illustrative embodiment of the invention.

In order to control oscillator 14 in chip IC2 to operate in synchronism with oscillator 14 in chip IC1, the junction of capacitor C2-1 and resistor R4-1 is connected to the input of chip IC2 which, when forced low, causes a pulse to be generated. It will be recalled in connection with the description of chip IC1 that an oscillator pulse is generated whenever the potential at the input connected to the junction of resistor R3-1 and capacitor C2-1 falls low enough, and that whenever a pulse is generated a negative potential appears at the junction of capacitor C2-1 and resistor R4-1. By extending this negative potential to the corresponding input of chip IC2, oscillator 14 in chip IC2 responds in synchronism with oscillator 14 in chip IC1—with an inter-pulse interval of 580 milliseconds during the measurement mode of operation.

A major difference between the connections to the two chips is that there are no components for chip IC2 comparable to resistors R2-1 through R4-1, and capacitors C2-1 and C5-1. The "oscillator" 14 in chip IC2 does in fact not function as an astable oscillator. Output rate limit gate 16 in chip IC2 does not function at all (due to the provision of resistor R5-2 without a corresponding capacitor C5-2), and the oscillator in chip IC2 does not function on its own; instead, oscillator 14 in chip IC2 is slaved to "master" oscillator 14 in chip IC1, with all pulses generated in chip IC2 being extended to voltage doubler 18. In effect, chip IC2 is a slave to chip IC1.

Figure 4:
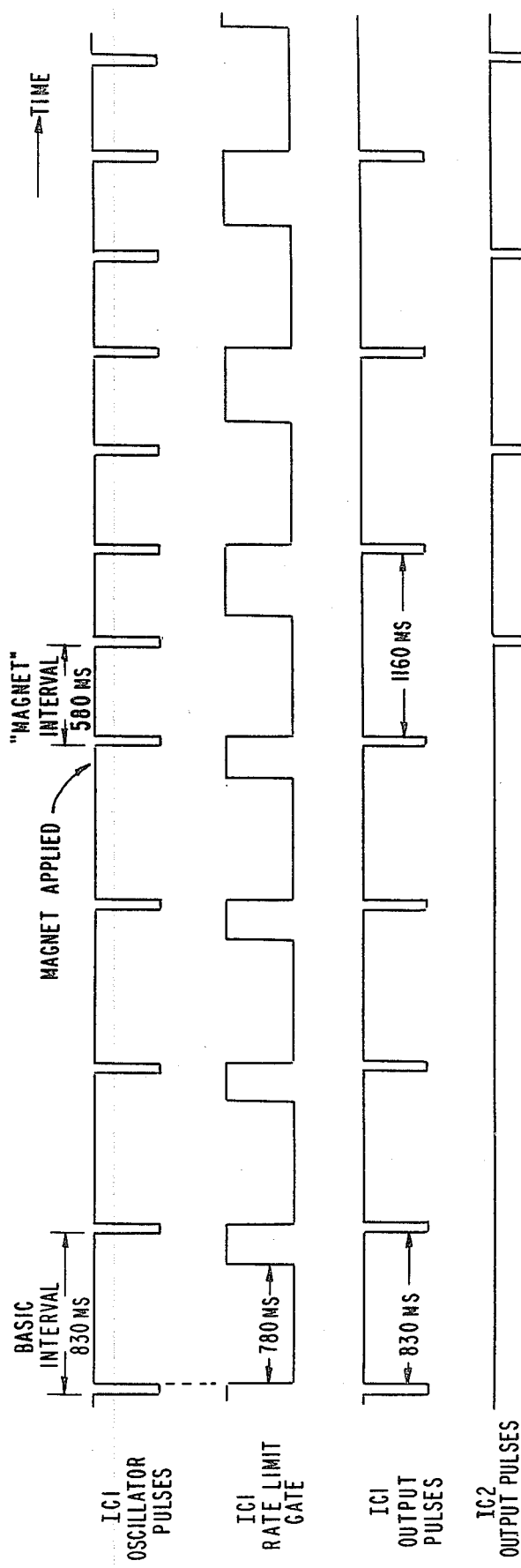
FIGS. 4 and 5 are timing waveforms which will be helpful in understanding the invention.

The reasons for the different connections will be apparent by referring once again to FIG. 4. The top line depicts the oscillator pulses generated by chip IC1. When the external magnet is held over switch 52, as shown in the top waveform, the inter-pulse interval is reduced from 830 milliseconds to 580 milliseconds. The second waveform depicts the operation of the output rate limit gate in chip IC1. It is now apparent that with the reduced inter-pulse interval (i.e., with a higher oscillator rate of about 103 pulses per minute), every other oscillator pulse in chip IC1 is blocked by output rate limit gate 16. Once the magnet is applied, every other oscillator pulse occurs when the second waveform in FIG. 4 is low in potential. Consequently, once the magnet is applied, what happens is that only every other oscillator pulse in chip IC1 results in the generation of an output pulse, as shown in the third waveform. Since the oscillator pulses occur at intervals of 580 milliseconds, output pulses occur at 1160-millisecond intervals.

The fourth waveform on FIG. 4 depicts the operation of chip IC2. As described above, during normal pacing (left side of FIG. 4), chip IC2 does not generate any output pulses because it is operated in the inhibit mode; the very generation of output pulses by chip IC1 prevents chip IC2 from doing the same. But when the system is operated in the measurement mode, every other oscillator pulse in chip IC1 does not result in an output pulse. Thus whenever chip IC1 generates an oscillator pulse that does not get through the output rate limit gate, chip IC2 can emit an output pulse. And because the oscillator circuit in chip IC2 is slaved to the oscillator in chip IC1, and the output rate limit gate 16 in chip IC2 does not function at all, it is apparent that whenever an oscillator pulse in chip IC1 is blocked, the simultaneous pulse in chip IC2 results in an output pulse. Thus, the third and fourth waveforms in FIG. 4 show pulses from the two chips occurring alternately. The pulses are fed alternately through diodes D4 and D5 to electrode 50, and thus output pulses appear on the electrode at 580-millisecond intervals, or at a rate of about 103 pulses per minute.

Figure 3C:
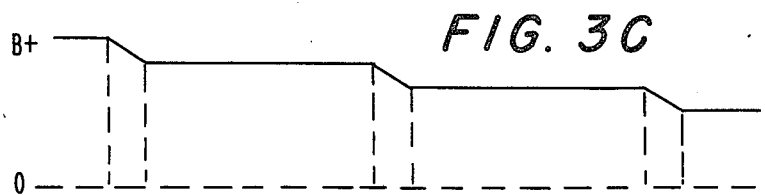

There is a big difference, however, between the two types of pulses. The pulses from chip IC1 are full-magnitude pulses because capacitors C3-1 and C4-1 fully charge between pulses in the normal way, as described above in connection with FIG. 3A. As shown in FIG. 3B, the voltage across each capacitor reaches the full battery potential by the time the next pulse is required. But because diode D3 is reverse biased when chip IC2 is called into play, there is no longer a charging potential for capacitors C3-2 and C4-2. These two capacitors initially charge just as do capacitors C3-1 and C4-1 while the pacer is operated in the normal mode; diode D3 is forward biased and switch 52 extends the full battery potential to resistors R6*-2 and R7*-2. Thus just prior to the transfer of switch 52, both capacitors are fully charged. But once the system starts to operate in the measurement mode, there is no longer a charging source for the capacitors. With the outputting of each output pulse from chip IC2, some of the charge on each capacitor is lost. FIG. 3C depicts the voltage across either one of these capacitors as a function of time. It is apparent that the capacitor voltage decreases as each output pulse is emitted by chip IC2, and the capacitor voltage remains at its new lower level between successive pulses. (Unlike prior art systems in which threshold measurements are made by causing successive pulses to be reduced in amplitude by the same decrement, in the system of our invention successive decrements are different. That is because each decrement is proportional to the total capacitor charge at the start of a pulse; while the percentage change is relatively constant for each pulse, the magnitude of each change depends on the initial charge and the electrode impedance. In fact, this is why the impedance measurement technique, to be described below, works in the first place.)

Figure 5:
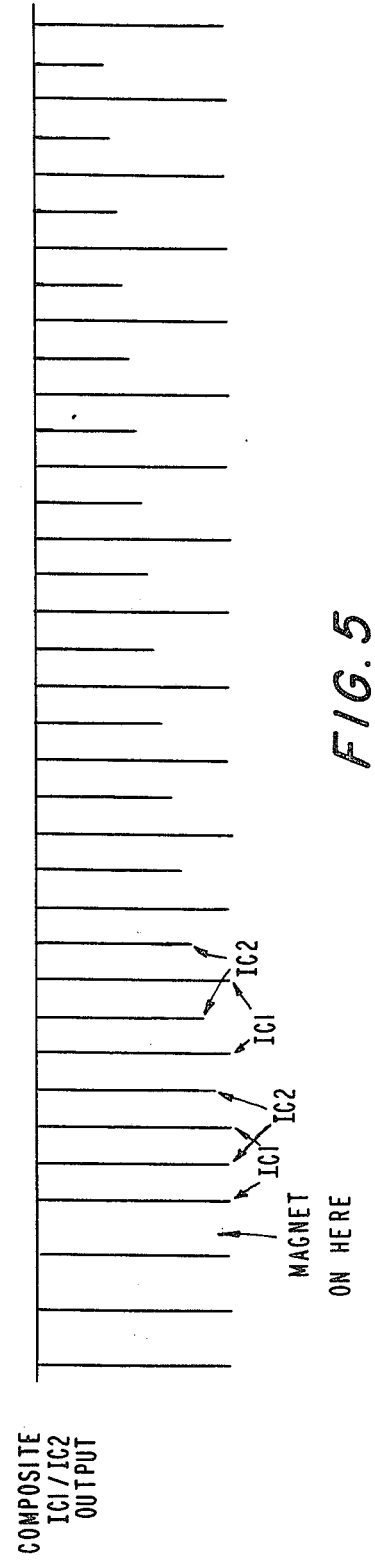

The net effect of operating the pacer in the measurement mode is depicted in FIG. 5. (The scale of FIG. 5 is compressed relative to that of FIG. 4.) At the left side of the waveform, before the magnet is applied, chip IC2 does not generate any pulses. Chip IC1 operates in the normal mode with output pulses being generated at 830-millisecond intervals (assuming that spontaneous heartbeats do not occur at a rate faster than 72 beats per minute). But as soon as the magnet is applied, the oscillator rate increases so that oscillator pulses are now generated at 580-millisecond intervals. However, it is only every other pulse from each chip which is extended to the electrode, the two chips feeding pulses alternately. All of the IC1 pulses are full-amplitude pulses, as depicted in FIG. 5, because capacitors C3-1 and C4-1 fully recharge between pulses. But the alternate IC2 pulses are continuously reduced in amplitude because capacitors C3-2 and C4-2 are not allowed to recharge between the outputting of IC2 pulses. It is thus apparent that the use of chip IC2, which is the same as chip IC1, results in a totally new function. Moreover, whatever measurements are taken are at no risk to the patient. Even if it takes minutes for the reducing-amplitude pulse sequence to finish, full-amplitude pacing pulses are generated at 1160-millisecond intervals.

Figure 6:
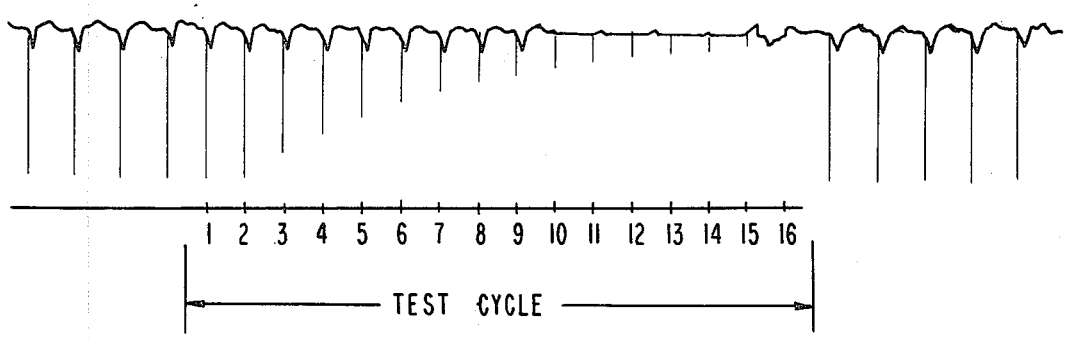
FIG. 6 depicts a prior art type EKG trace obtained during a threshold check.

FIG. 6 depicts the manner in which threshold measurements were made in the prior art. With the application of an external magnet, the amplitudes of the generated pulses continuously decrease. Over a test cycle of sixteen pulses (which occur at a fixed rate, just as they do in the illustrative embodiment of the invention), the larger-amplitude pulses results in capture while the lower-amplitude pulses do not. By observing an EKG trace, on which the generated pulses and the heartbeat signals both appear, it is easy enough to determine the threshold level. In the waveform of FIG. 6, it is apparent that capture was lost between the ninth and tenth pulse amplitudes of the test cycle. The problem with this prior art approach is that toward the end of the test cycle the patient's heart is not beating (unless it can do so spontaneously). In order to avoid a dangerous situation, the test cycle must be limited in duration; but even so, in the worst case 15 heartbeats will be absent. Furthermore, since the pulse amplitude must decrease from maximum to minimum (zero) during only sixteen pulses, it is apparent that there is limited resolution (one-sixteenth of full scale) in any threshold determination.

Much more accurate results can be obtained if successive pulse amplitudes differ only slightly. Although not shown in FIG. 5, in actual practice 30, 40 or even 50 successive pulses from chip IC2 may be required to measure the threshold, thus giving much greater resolution without any danger to the patient because full-amplitude pulses are generated by chip IC1 at a rate slightly in excess of 50 pulses per minute. Even if the magnet is held over the chest of the patient indefinitely, there is no danger. Of course, there is no need to hold the magnet in place once capture is lost. But if the magnet is not removed, while eventually capacitors C3-2 and C4-2 completely discharge and chip IC2 no longer delivers stimulating pulses at all, chip IC1 still delivers full-amplitude pulses at a rate slightly above 50 per minute, as shown at the right side of FIG. 5.

Figure 7:
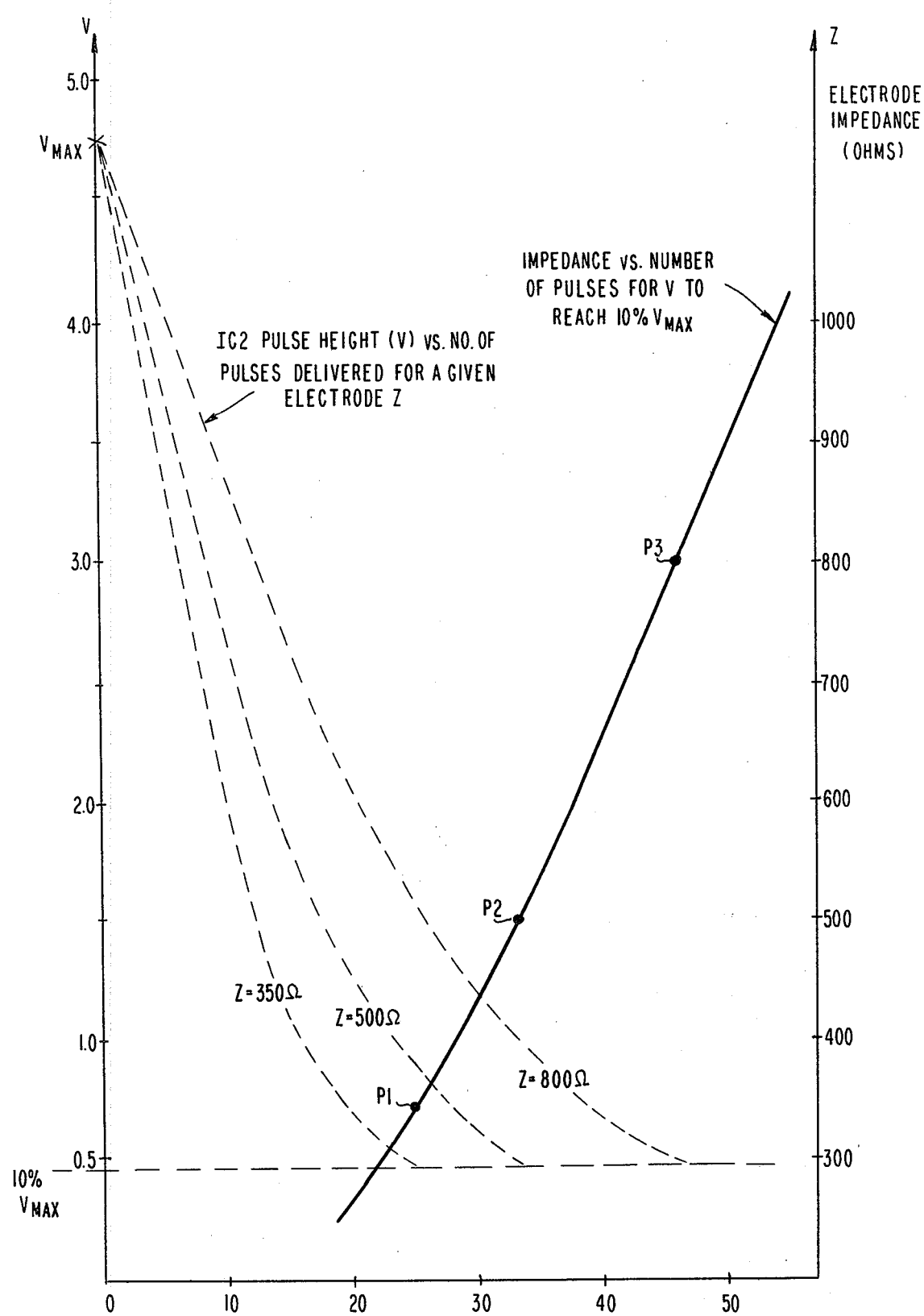
FIG. 7 is a chart which may be used with the pacer of FIGS. 1 and 2 for determining electrode impedance.

In addition to allowing high-resolution threshold measurements to be made, the pacer of our invention also allows high-resolution electrode impedance measurements to be made. FIG. 7 depicts a plot which may be furnished to the physician. (The leftmost Y axis as well as the three dashed lines are not included on the plot furnished to end users; they are utilized as will be described below, to derive the solid line.) The rightmost Y axis represents the electrode impedance, measured in ohms. The horizontal axis represents the number of pulses from chip IC2 which are required for the pulse height to drop from its full amplitude to ten percent of this value. The physician looks at the skin potential recording (or other means for measuring pulse amplitude) and measures the maximum pulse amplitude. He then determines which of the pulses in the reducing-amplitude sequence is closest to ten percent of the maximum value, and lastly he counts the number of pulses in the reducing-amplitude sequence (not the full-amplitude pulses in between). Suppose this number is 35. The physician looks at the plot of FIG. 7 and determines that associated with an X axis value of 35, the electrode impedance is 525 ohms.

The reason that this works, and the way in which the plot may be derived, is as follows. A pacer (which is not implanted in a patient) is connected across an impedance of known value and a trace is made of the IC2 pulse heights while a magnet is held over the reed switch. A curve is then drawn of pulse height versus pulse count. The same thing is done for other known impedances. Three such curves are shown by the dashed lines in FIG. 7, for impedances of 350, 500 and 800 ohms. (For example, when an impedance of 350 ohms was used, the pulse height was about 2.1 volts on the tenth pulse.) As successive pulses are generated, the pulse height drops down from $V_{MAX}$, and eventually reaches zero. Depending upon the value of $V_{MAX}$, a horizontal line is then drawn corresponding to ten percent of this value. This line intersects the 350-ohm curve where the pulse count is 25. What this means is that for an impedance of 350 ohms connected to the pacer output, the IC2 pulse height is reduced to ten percent of its maximum value after 25 pulses have been emitted. Point P1 is plotted to have an X axis value of 25 counts and a Y axis value of 350 ohms. In a similar manner, points P2 and P3 are plotted for the two other curves, to indicate for each respective impedance value the number of pulses required for the pulse height to be reduced to ten percent of its maximum value. The solid curve is then derived by connecting the three points P1, P2 and P3 (and any others which may be plotted in a comparable way).

In effect, what the physician is doing is just the reverse. He counts the number of pulses which result in an amplitude drop by a predetermined factor (90%), and he uses the plot to determine the corresponding electrode impedance. Because successive pulses from chip IC2 are reduced only slightly in amplitude, the resolution is very high. With reference to FIG. 7, over an effective pulse-count range of 30 (20—50), there is an impedance range of about 600 ohms. Thus the impedance can be determined to about 20 ohms of its actual value, on average.

Another way to derive the solid curve of FIG. 7, a way which is more direct and therefore better, is simply to place a set of known impedances between the electrode and ground, and in each case to count the number of pulses from chip IC2 required for the pulse amplitude to fall to 10% of its starting voltage ($V_{MAX}$). A plot may then be made directly of the number of pulses versus test impedance.

It is important to appreciate that this technique allows the electrode impedance to be determined without requiring any knowledge of the actual magnitude of the maximum pulse amplitude. Although there are techniques for measuring battery potential, and thus the maximum pulse amplitude, the actual value is not necessary for measuring electrode impedance. (If a quantitative value for the threshold measurement is desired, then the actual battery potential must be determined, as it has to be determined with prior art systems. Test systems, in which pacer rate becomes a function of battery potential, are well known in the art. In fact, the illustrative embodiment of the invention functions that way.) No matter what the initial charge across each of capacitors C3-2 and C4-2, it will still take the same number of pulses for the potential across each capacitor to be reduced to ten percent of the initial value. For this reason, even in the dashed line portion of FIG. 7, actual values of pulse heights need not be determined. All that matters is the relative amplitude of each pulse as compared to the pulse of maximum amplitude. If a battery with a different potential is used to derive the dashed curves of FIG. 7, the results will be different since all of the curves will start at a different $V_{MAX}$ value. But the intersections with the 10% $V_{MAX}$ line will still be the same because it will still require the same number of pulses for the pulse amplitude to be reduced to ten percent of its maximum value for each impedance, and thus the three points P1, P2 and P3 will remain the same. What this means is that the physician also need have no concern for actual pulse amplitudes; accurate impedance measurements may be made based solely on relative pulse amplitudes.

Prior art threshold measurement pacers did not allow impedance measurements to be made. This is because the decrements in successive pulse amplitudes were not a function of electrode impedance. But in the pacer of our invention, the decrements are directly proportional to electrode impedance. The absolute values of the decrements depend on the initial charge across the capacitors in the output circuit and the impedance, but the percentage difference between successive pulses depends only on the impedance; the amplitudes of every pair of successive pulses differ by the same fixed percentage. This is the key to impedance measurement. If the amplitude differences are unrelated to impedance, as in the prior art, then the resulting EKG trace, while it can provide threshold measurement information, can give no indication of electrode impedance.

There is nothing unique about a 10% level, and what could be looked for is the reduction in pulse amplitude to 20% of the maximum value. Of course, the physician would have to consult a plot which was derived by counting the number of pulses required for the pulse amplitude to decrease to 20% of its maximum value for each of known impedance values. Similarly, the pulse count on the plot could represent all pulses, not only those in the decreasing-amplitude sequence, which would simply change the scale of the X axis.

It should also be noted that the number of pulses required for the pulse amplitude to decrease to any percentage of its initial value depends upon the pulse width; the wider the pulses, the more charge lost during the delivery of each pulse. This simply means that a separate plot should be provided for each possible pulse width if a particular pacer includes a mechanism for changing pulse width.

Although it is contemplated that the physician will be provided with a plot of the form of FIG. 7, he could alternatively be given a data sheet listing an impedance value for each pulse count. In general, any form of "chart" will suffice, be it a plot, a set of data or anything else, as long as it conveys an impedance value for each pulse count.

For impedance-measuring purposes, it is not essential that the alternate-pulse feature of our invention be employed; it is possible not to provide full-amplitude pulses between reducing-amplitude pulses. The impedance-measuring technique does not require the provision of full-amplitude pulses during the measurement cycle. But it is better to provide them because it allows many more pulses of reducing amplitude to be generated (i.e., a smaller difference between successive pulses) without danger to the patient, and thus much higher resolution. If what is looked for is a reduction in pulse amplitude down to 10% of the maximum value, invariably capture will be lost and the patient will be left without pacer support while the measurement is being conducted. It is also possible to provide a pulse sequence alternation scheme on other than a one-for-one basis. For example, the sequence of reducing-amplitude pulses could alternate with the sequence of constant-amplitude pulses, with two pulses in the latter sequence separating successive pulses in the former sequence. The "test" sequence still has decreasing amplitudes even though its pulses are separated by two, rather than only one, constant-amplitude pulses.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What we claim is:

1. A system for measuring pacer electrode impedance comprising a pacer including means for delivering stimulating pulses to a connected electrode, and externally controlled means for causing at least some of said stimulating pulses to be delivered in a sequence having decreasing amplitudes; and a chart associated with said pacer which depicts electrode impedance as a function of the number of said at least some stimulating pulses required for the amplitudes thereof to decrease by a predetermined factor.

2. A system in accordance with claim 1 wherein said chart conforms to the numbers of said at least some stimulating pulses required for the amplitudes in several sequences to decrease by the same predetermined factor for several respective impedances of known values to which said pacer is caused to deliver stimulating pulse sequences.

3. A system in accordance with claim 2 wherein said pulse delivering means includes a first pulse generator having a capacitor, means for discharging said capacitor into said connected electrode, and means for recharging said capacitor; and said externally controlled means inhibits the recharging of said capacitor for the duration of a pulse sequence during which electrode impedance is measured such that the pulses generated by said first pulse generator have successively decreasing amplitudes.

4. A system in accordance with claim 3 wherein said pulse delivering means includes a second pulse generator for generating stimulating pulses of constant amplitude which alternate with said stimulating pulses having successively decreasing amplitudes.

5. A system in accordance with claim 4 wherein said second pulse generator includes means normally operative to control the generation of stimulating pulses at a first rate for normal pacing of a patient's heart, and rate-changing means responsive to the operation of said externally controlled means for controlling the generation of stimulating pulses at a second lower rate.

6. A system in accordance with claim 5 wherein said normally operative means includes a pulse oscillator operating at said first rate, means for blocking any pulse from said oscillator which occurs within a predetermined time interval following a preceding pulse, said predetermined time interval being short enough such that during normal pacing none of said oscillator pulses are blocked, and means for controlling the delivery of a stimulating pulse to said connected electrode for each oscillator pulse which is not blocked; and said rate-changing means includes means for increasing the rate of said pulse oscillator to a third higher rate which results in the blocking of alternate oscillator pulses such that said stimulating pulses are delivered to said connected electrode at said second lower rate.

7. A system in accordance with claim 6 further including means for disabling operation of said first pulse generator during normal pacing under control of said second pulse generator.

8. A system in accordance with claim 7 further including means for controlling the rate of said first pulse generator to equal the rate of said second pulse generator.

9. A system in accordance with claim 7 wherein said disabling means includes means responsive to each stimulating pulse from said second pulse generator for preventing the operation of said first pulse generator, such that (a) during normal pacing, every stimulating pulse from said second pulse generator disables the operation of said first pulse generator so that no stimulating pulses are delivered by said first pulse generator, and (b) responsive to the operation of said externally controlled means, said first pulse generator is disabled from operating only on alternate pulses from said pulse oscillator when said second pulse generator delivers stimulating pulses to said connected electrode.

10. A system in accordance with claim 9 wherein the active circuits in each of said pulse generators are contained on a single chip, and the active circuits in the two chips are identical.

11. A system in accordance with claim 1 wherein said stimulating pulse delivering means includes a first normally inoperative pulse generator, responsive to the operation of said externally controlled means, for emitting pacing pulses having continuously decreasing amplitudes; and a second pulse generator for generating constant-amplitude pulses interspersed with the pulses having continuously decreasing amplitudes emitted by said first pulse generator.

12. A system in accordance with claim 11 wherein said second pulse generator normally generates pulses at a first rate and, responsive to operation of said externally controlled means, generates pulses at a second lower rate.

13. A system in accordance with claim 11 wherein the active circuits in each of said pulse generators are contained on a single chip, and the active circuits in the two chips are identical.

14. A pacer which facilitates the measurement of pacer electrode impedance comprising means for delivering stimulating pulses to a connected electrode, externally controlled means for causing at least some of said stimulating pulses to be delivered in a sequence having decreasing amplitudes, and means for causing the amplitude of each of said at least some stimulating pulses to be less than that of its predecessor by a precentage which is directly proportional to the impedance of said connected electrode.

15. A pacer in accordance with claim 14 wherein said pulse delivering means includes a first pulse generator having a capacitor, means for discharging said capacitor into said connected electrode, and means for recharging said capacitor; and said externally controlled means inhibits the recharging of said capacitor for the duration of a pulse sequence during which electrode impedance is measured such that the pulses generated by said first pulse generator have successively decreasing amplitudes.

16. A pacer in accordance with claim 15 wherein said pulse delivering means includes a second pulse generator for generating stimulating pulses of constant amplitude which alternate with said stimulating pulses having successively decreasing amplitudes.

17. A pacer in accordance with claim 16 wherein said second pulse generator includes means normally operative to control the generation of stimulating pulses at a first rate for normal pacing of a patient's heart, and rate-changing means responsive to the operation of said externally controlled means for controlling the generation of stimulating pulses at a second lower rate.

18. A pacer in accordance with claim 17 wherein said normally operative means includes a pulse oscillator operating at said first rate, means for blocking any pulse from said oscillator which occurs within a predetermined time interval following a preceding pulse, said predetermined time interval being short enough such that during normal pacing none of said oscillator pulses are blocked, and means for controlling the delivery of a stimulating pulse to said connected electrode for each oscillator pulse which is not blocked; and said rate-changing means includes means for increasing the rate of said pulse oscillator to a third higher rate which results in the blocking of alternate oscillator pulses such that said stimulating pulses are delivered to said connected electrode at said second lower rate.

19. A pacer in accordance with claim 18 further including means for disabling operation of said first pulse generator during normal pacing under control of said second pulse generator.

20. A pacer in accordance with claim 19 further including means for controlling the rate of said first pulse generator to equal the rate of said second pulse generator.

21. A pacer in accordance with claim 19 wherein said disabling means includes means responsive to each stimulating pulse from said second pulse generator for preventing the operation of said first pulse generator, such that (a) during normal pacing, every stimulating pulse from said second pulse generator disables the operation of said first pulse generator so that no stimulating pulses are delivered by said first pulse generator, and (b) responsive to the operation of said externally controlled means, said first pulse generator is disabled from operating only on alternate pulses from said pulse oscillator when said second pulse generator delivers stimulating pulses to said connected electrode.

22. A pacer in accordance with claim 21 wherein the active circuits in each of said pulse generators are contained on a single chip, and the active circuits in the two chips are identical.

23. A pacer in accordance with claim 14 wherein said stimulating pulse delivering means includes a first normally inoperative pulse generator, responsive to the operation of said externally controlled means, for emitting pacing pulses having continuously decreasing amplitudes; and a second pulse generator for generating constant-amplitude pulses interspersed with the pulses having continuously decreasing amplitudes emitted by said first pulse generator.

24. A pacer in accordance with claim 23 wherein said second pulse generator normally generates pulses at a first rate and, responsive to operation of said externally controlled means, generates pulses at a second lower rate.

25. A pacer in accordance with claim 23 wherein the active circuits in each of said pulse generators are contained on a single chip, and the active circuits in the two chips are identical.

* * * * *